United States Patent [19]

Hattori

[11] 4,344,682
[45] Aug. 17, 1982

[54] DATA RECORDING DEVICE

[75] Inventor: Shinichiro Hattori, Tokyo, Japan

[73] Assignee: Olympus Optical Co., Ltd., Tokyo, Japan

[21] Appl. No.: 217,232

[22] Filed: Dec. 17, 1980

[30] Foreign Application Priority Data

Dec. 27, 1979 [JP] Japan .................................. 54/172005

[51] Int. Cl.³ ........................ G03B 1/18; G03B 17/24; G03B 29/00
[52] U.S. Cl. .................................... 354/62; 354/106; 354/173
[58] Field of Search ................. 354/62, 173, 217, 218, 354/105–109; 355/39, 40, 41; 352/55; 346/107 R, 107 A

[56] References Cited

U.S. PATENT DOCUMENTS

| | | | |
|---|---|---|---|
| 3,722,991 | 3/1973 | Edhlund | 355/40 X |
| 3,772,465 | 11/1973 | Vlahos et al. | 355/40 X |
| 3,819,854 | 6/1974 | Kolb | 355/40 X |
| 3,953,868 | 4/1976 | Kawamura et al. | |
| 3,987,467 | 10/1976 | Cowles | 354/105 |
| 4,053,909 | 10/1979 | Shinoda et al. | 354/105 |
| 4,167,315 | 9/1979 | Nanba et al. | 354/106 |
| 4,192,597 | 3/1980 | Ting | 354/62 X |

FOREIGN PATENT DOCUMENTS 2449093 4/1975 Fed. Rep. of Germany .

OTHER PUBLICATIONS

JP-A-55-57836 (Pat. Abstract of Japan, vol. 4, No. 100, Jul. 18, 1981, p. 6P19).

Primary Examiner—L. T. Hix
Assistant Examiner—William B. Perkey
Attorney, Agent, or Firm—Frishauf, Holtz, Goodman and Woodward

[57] ABSTRACT

A keyboard is connected to a data recording section through a memory circuit and a read-out section. A film is mounted in a dark box in the vicinity of the data recording section. The film is connected to a frame-number setting dial through film-winding sections and a control circuit. All the recorded data input by the keyboard are stored in the memory circuit. The recorded data corresponding to the frame number specified by the frame-number setting dial is output by the read-out section as well as displayed at a display section. Simultaneously, the film is wound for exposure independently of the frame arrangement order so that the specified frame comes to a predetermined position in response to the frame numbersetting dial.

7 Claims, 4 Drawing Figures

F I G. 1
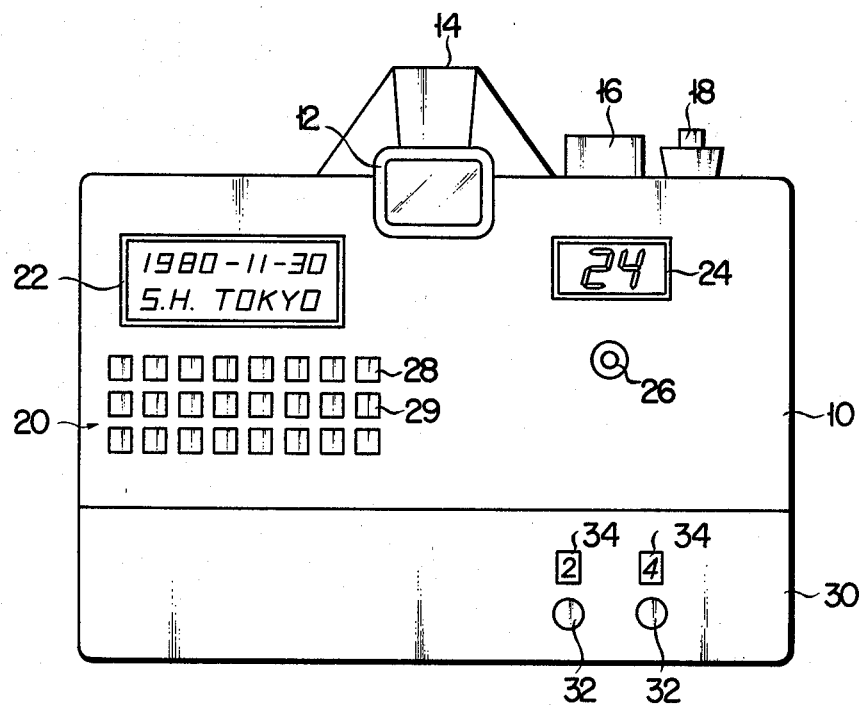

DATA RECORDING DEVICE

BACKGROUND OF THE INVENTION

The present invention relates to a data recording device for recording information such as letters and numerals on film.

A conventional data recording device, for example, a data recording device built in a camera, has a signal generating section comprising a keyboard for inputting data and a data recording section consisting of a light emitting diode and so on, and is so constructed that the data input from the keyboard is recorded on film in a manner similar to conventional photography. With such a conventional device, the user operates the keyboard before taking each photograph to input the desired data such as date, person's name etc., and presses the shutter release button of the camera thereafter. The time required for this keyboard operation becomes longer according to the amount of data to be input. As a result, in the camera with the conventional data recording device, there is a danger of failing to take a desired photograph due to a loss of a subject. Further, since the data to be recorded must be set by the user before taking each photograph, there is a danger of errors occuring when there is not much time before taking a photograph, that is, when the time allowed for operating the keyboard is short. Further, even when such errors have occurred, the user may not be aware of such an error so that erroneous data may be recorded on the film. When photographs must be continuously taken a number of times within a certain period of time under the same conditions (for example, when photographing the respective parts of the body cavity of a patient with an endoscope photography device), the user must repeat the same keyboard operation each time. Thus, this prior device is defective in that extra time is needlessly consumed for taking photographs.

It is, therefore, the primary object of the present invention to provide a data recording device which is capable of recording desired data with ease on a desired frame of a film and of easily correcting erroneous data when it is discovered.

SUMMARY OF THE INVENTION

A data recording device of the present invention has means for generating data corresponding to a frame and data to be recorded, memory means for storing this data, and means for reading out the data stored in the memory means. The device further includes frame-specifying means for generating a signal corresponding to a desired film frame, means for driving the film, and means for recording the desired data on the film. When the desired frame is specified by the frame-specifying means, the desired film frame is located at a predetermined position. Simultaneously, the data corresponding to the frame specified by the frame-specifying means is read out from the memory means by the read-out means, and is recorded on the specified film frame by the recording means.

BRIEF DESCRIPTION OF THE DRAWINGS

FIG. 1 is a rear view of a camera in which a data recording device according to an embodiment of the present invention is built in;

FIG. 3 is an overall view of an endoscope photography apparatus in which a data recording device according to another embodiment of the present invention is built in.

DESCRIPTION

Figure 2:
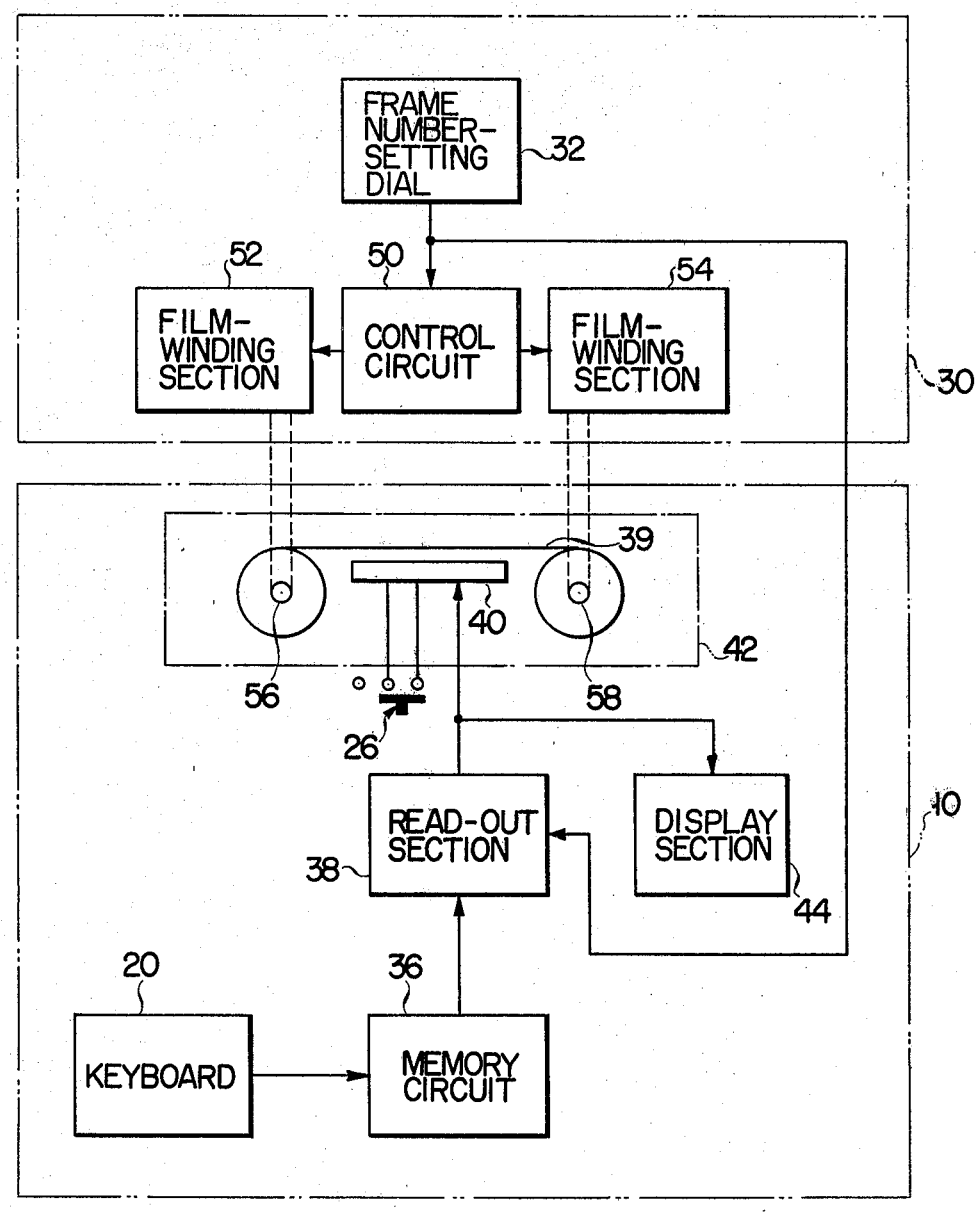
FIG. 2 is a block diagram of the embodiment shown in FIG. 1.

A data recording device according to an embodiment of the present invention as shown in FIGS. 1 and 2 is used for a camera, for example, a single lens reflex camera. A viewfinder 12 is disposed at the upper part of the rear surface of a camera main body 10 as shown in FIG. 1, and at the upper part of the main body 10 are disposed a pentaprism portion 14 for housing a pentaprism (not shown), a film speed setting dial 16, and a release button 18. At the rear surface of the main body 10 are also disposed a keyboard 20 constituting a signal generating section, a data indicator 22 comprising a liquid crystal display (to be referred to as an LCD hereinafter), a frame number indicator 24 and a recording starting button 26. The keyboard 20 includes key buttons 28, 29, . . . each corresponding to letters, numerals, symbols and so on. A bottom case 30 is detachably mounted to the camera main body 10 and has a frame number-setting dial 32 and a display window 34.

Description is now given with reference to the block diagram shown in FIG. 2 of one embodiment of this invention. The output terminal of the keyboard 20 is connected to the input terminal of a circuit 36, and the output terminal of the memory circuit is connected to one input terminal of a read-out section 38. The output terminal of the read-out section 38 is connected to one input terminal of a data recording section 40 provided together with a film 39 inside a dark box 42 disposed inside the camera main body 10. To the other input terminals of the data recording section 40 is connected the recording starting button 26, and the data recording section 40 can be operated independently of the release button 18 by the recording starting button 26. The output terminal of the read-out section 38 is also connected to a display section 44 consisting of the data indicator 22 and the frame number indicator 24 (FIG. 1). The memory circuit 36 comprises, for example, a semiconductor memory or a magnetic bubble memory with a memory capacity sufficient for storing at least all of the data to be recorded in the frames in addresses corresponding to the respective frames of the film 39. Accordingly, once identification codes (for example, frame numbers) of every frame of the film 39 and the data to be recorded corresponding to the frame numbers are input in the memory circuit 36, the memory circuit 36 stores all of the input information for a required period of time, for example, until the information is read out by the read-out section 38. The data recording section 40 comprises a control circuit and a light emitting section which consists of a light emitting diode or an LCD, and a lamp. The section 40 reproduces the data transmitted from the read-out section 38 into letters (e.g., alphabets), numerals, symbols and so on and records them in the corners of the frame of the film 39 at the predetermined position such as the exposing position.

An output terminal of the frame number-setting dial 32 arranged at the bottom case 30 is connected to the other output terminal of the read-out section 38 as well as to an input terminal of a control circuit 50. The control circuit 50 is connected to film-driving means, for example two output terminals of the control circuit 50 are connected to the input terminals of first and second film-winding section 52 and 54 which serve as the film-driving means, respectively. The control circuit 50 and the first and second film-winding sections 52 and 54 are provided inside the bottom case 30. The first and second film-winding sections 52 and 54 each comprise motors, gears, brakes and so on (not shown) and are mechanically coupled to winding shafts 56 and 58 of the film 39. The frame number-setting dial 32 comprises, for example, a rotary switch. When a desired film frame number, for example "24" is set by the frame number-setting dial, the specified or selected frame number, i.e., "24" is displayed at the display window 34 (FIG. 1) by a numeral plate (not shown) rotated in cooperation with the frame number-setting dial 32. The control circuit 50 comprises a microprocessor, for example, which has a frame position detecting circuit, a comparator, a control signal generating circuit and so on (not shown). The frame position detecting circuit measures the film feed amount, taking the first frame position of the mounted film 39 as a reference, and transmits a frame position detecting signal to the control signal generating circuit and the comparator. The comparator is so constructed that it outputs a predetermined comparing signal to the control signal generating circuit when the frame number selected by the frame number-setting dial 32 and the frame position data of the frame position detecting circuit correspond with each other. The control signal generating circuit transmits an operation instruction signal and a stop signal (i.e., a control signal) to the first and second film-winding sections 52 and 54 in response to the frame position detecting signal and the comparing signal. The film 39 is so wound that the frame corresponds to the number set at the frame setting dial 32 by the control circuit 50 and the first and second film winding sections 52 and 54. This film 39 is wound in both directions, i.e., in the forward and reverse directions. When the frame of the film 39 specified by the frame number-setting dial 32 comes to the exposing position, the control circuit 50 generates a stop signal, and the sections 52 and 54 stop in response to the stop signal. The method for detecting the frame position of the film 39 mounted in the dark box 42 is not limited to the method described above. For example, a hole for detecting the position of the frame is formed in correspondence with the respective frames of the film 39, and the positions of the respective frames may be detected by optically detecting the hole.

The data recording device of this construction is operated in the manner described below. First, when the photography plan such as the subject, photographing order and photographic conditions are determined in advance, the series of frame numbers and the data to be recorded corresponding to the frames are input in the memory circuit 36 from the keyboard 20. The frame number and the data input by the operation of the keyboard 20 are displayed at the display section 44, that is, the data indicator 22 and the frame number indicator 24 upon every operation. Thus, the user is able to visually confirm the keyboard operation. The keyboard operations are continued until the data corresponding to all of the frames of the film is completely input to the memory circuit 36. Photographing is begun after completing input of the data. The desired frame number is specified according to the subject and the photographing order by operating the frame number-setting dial 32, and the frame number is simultaneously displayed at the display window 34. When a desired frame number, for example "24", is specified, a signal corresponding to the frame number "24" is output from the frame number-setting dial 32, and transmitted to the control circuit 50. In response to this signal, the control circuit 50 generates the control signal (not shown) to the first and second film-winding sections 52 and 54. The film 39 is wound and fed by the film-winding sections 52 and 54 which operate in response to the control signal. When the frame of the film 39 corresponding to the number specified by the frame number-setting dial 32 comes to a predetermined position, for example, the exposing position, the control circuit 50 outputs the stop signal. In response to the stop signal, the film-winding sections 52 and 54 stop. Thus, the film frame having the number specified by the frame number-setting dial 32 is correctly positioned at the exposing position. Simultaneously, the specified frame number is displayed at the frame number indicator 24, and the data to be recorded corresponding to the specified frame is displayed at the data indicator 22. The data to be recorded may be visually confirmed. When there is no error contained in this data, the release button 18 is depressed and a photograph is taken. Subsequently, the recording starting button 26 is depressed, and the data is recorded on the specified frame of the film 39 by the data recording section 40. When there is an error in the data displayed at the data indicator 22 and there is sufficient time for correction of the error, the keyboard 20 is operated to correct the data. Thereafter, a photograph is taken by the same operation. When there is an error in the data displayed at the data indicator 22 and there is not sufficient time to correct such an error, the recording starting button 26 is not depressed, and a photograph is taken by depressing the release button 18. When there is enough time later, the correct data is recorded on the film 39 by the same operation as described above.

A case will now be described in which the photography plan such as the subject, the photographing order and the photographic conditions cannot be determined in advance. Under these circumstances, photographs are taken according to the general order of the frames of the film 39, and the data corresponding to the respective frames is recorded after exposing all of the frames. Thus, the frame numbers and the data to be recorded corresponding to these frames are recorded by the user (for example, by noting down or by recording the frame numbers and the data voiced by the user). After a series of operations, the keyboard 20 is operated according to the recorded information, and the frame numbers and the data are stored in the memory circuit 36. The recording starting button 26 is depressed thereafter. However, since the operation of the keyboard 20, the recording starting button 26 and so on is the same, the description will be omitted.

According to the first embodiment of the data recording device of the present invention having the construction as described above, the data input to the memory circuit 36 by the keyboard 20 is displayed at the display section 44 each time. When the desired film frame is set by the frame number-setting dial 32, the frame number and the data are also displayed at the display section 44. Accordingly, since the correctness of the data input to the memory circuit 36 may be easily confirmed by the user, errors in the data, if any, may be easily corrected. It may be prevented that an error included in the data is not detected by the user and directly recorded in the film frame. Further, since the recording starting button 26 operates independently of the release button 18, the data need not be recorded on the film 39 simultaneously with taking the photographs. The data may thus be recorded in the film 39 freely before or after taking the photographs with all the frames, depending on the individual photographing conditions. Therefore, a photograph may be taken independently of the input operation so that photographs may be taken fast and efficiently. Further, since any frame of the film 39 may be freely set to the exposing position independently of its order, by the frame-setting dial 32, the photographs need not be taken according to the order of the frames. Similarly, the data recording may be performed by selecting a desired frame independently of the order of the frames. The photographing and data recording operations may be freely performed by the user, thus widening the application of the device. Additionally, in this embodiment, the bottom case 30 is detachably mounted to the camera main body 10. However, it may be also possible that the frame number-setting dial 32, the control circuit 50 and film-winding sections 52 and 54, etc. are mounted in the camera main body 10 to provide a unit integral with the bottom case 30.

Figure 3:
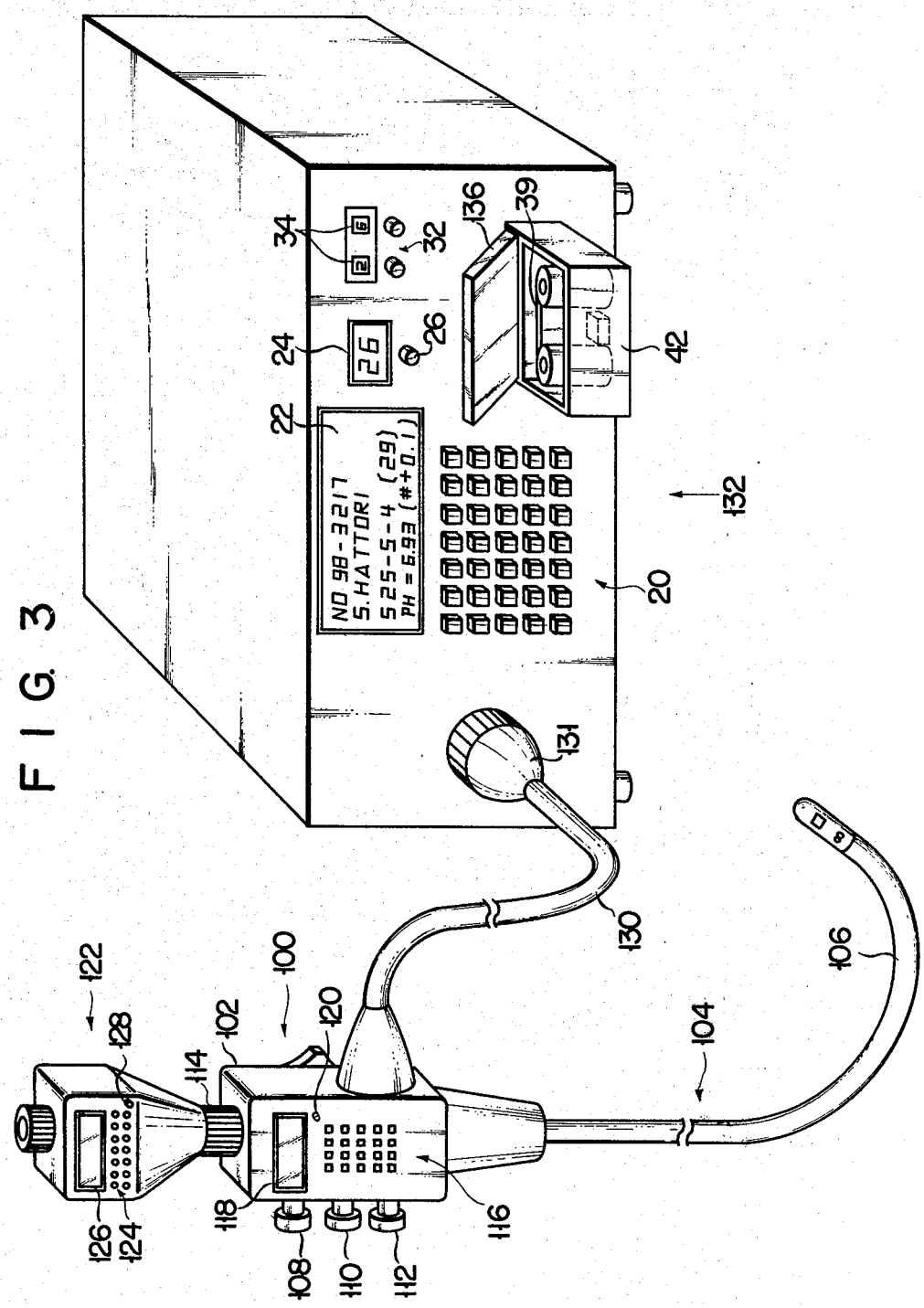
Figure 4:
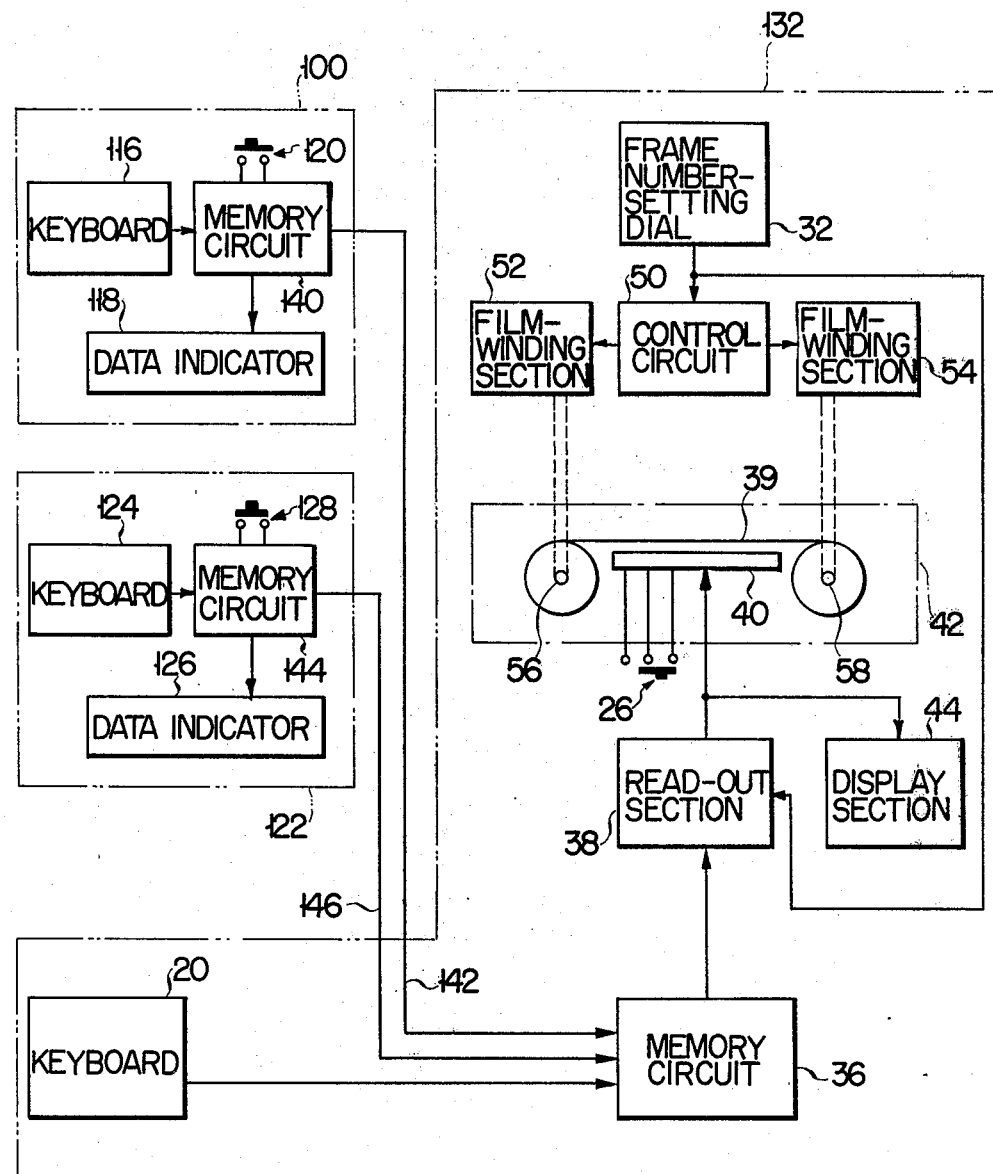
FIG. 4 is a block diagram of the embodiment shown in FIG. 3.

The data recording device according to another embodiment of the present invention shown in FIGS. 3 and 4 is applied to an endoscope photographing apparatus. An endoscope 100 comprises an operating section 102 and an insertion section 104. The operating section 102 includes an angle knob 108 for freely bending a flexible portion 106 of the insertion section 104, an air-feeding button 110, a water-feeding button 112, an ocular section 114, and so on. The operating section of the endoscope 100 further includes a first separate keyboard 116, a first separate data display indicator 118, and a first data transfer switch 120. An endoscope camera 122 mounted to the ocular section 114 also includes a second separate keyboard 124, a second separate data indicator 126, and a second separate data transfer switch 128. The operating section 102 of the endoscope 100 of this arrangement is coupled to a light supply apparatus 132 through a universal cord 130 and a socket 131. Inside the universal cord 130 are provided a light guide, an air-feeding tube, a water-feeding tube and so on (not shown). The light supply apparatus 132 includes a light source (not shown) for transmitting light to the endoscope 100. The light emitted from this light source is transmitted to the endoscope 100 through the light guide. The dark box 42 is mounted to the front panel of the light supply apparatus 132 and a lid 136 is mounted to the top of the dark box 42 in such a manner that it is free to open and close. The film 39 for the endoscope camera 122 is encased inside the dark box 42. On the front panel of the light supply apparatus 132 are mounted the keyboard 20, the data indicator 32, the frame number indicator 14, the recording starting button 26, the frame number-setting dial 32, and the display window 34. Since they are of the same construction as that shown in FIGS. 1 and 2, the description will be omitted.

Description is now given with reference to the block diagram of another embodiment of this invention shown in FIG. 4. The output terminal of the first separate keyboard 116 mounted in the endoscope 100 is connected to the input terminal of the first separate memory circuit 140. One output terminal of the memory circuit 140 is connected to the display indicator 118, and the other output terminal is connected to one input terminal of the memory circuit 36 disposed inside the light supply apparatus 132. The first data transfer switch 120 is connected to the first separate memory device 140. When the switch 120 is set to on, the data input to the memory circuit 140 by the keyboard 116 is transmitted to the memory circuit 36 disposed in the light supply apparatus 132. Similarly, the second separate keyboard 124 disposed in the endoscope camera 122 is connected to the memory circuit 36 inside the light source device 132 through the second separate memory circuit 144 and an external connection wire 146. Similarly, the second separate data indicator 126 and the second data transfer switch 128 are connected to the second separate memory circuit 144. The external connecting wires 142 and 146 are encased inside the universal cord 130. The other parts are the same as shown by the block diagram of the embodiment shown in FIG. 2, so that the description thereof will be omitted.

Description is now given of an operation of a data recording device according to another embodiment of the invention which is arranged as described above. Before or after taking a photograph of the body cavity of a patient, the film frame number and the data to be recorded corresponding to the frame are input by the keyboard 20 in the memory circuit 36 and stored therein. After the film 39 is mounted in the dark box 42 and the lid 136 is closed, the data is recorded in the respective frames of the film 39 using the frame number setting dial 32 according to the procedure in the case of the embodiment of FIG. 1. In this procedure, the first separate keyboard 116 and the first separate memory circuit 140 mounted in the endoscope 100, and the second separate keyboard 124 and the second separate memory circuit 144 mounted in the endoscope camera 122 need not be used. However, when the endoscope 100 is used in combination with the conventional light supply apparatus which does not have the data recording device with the keyboard 20 and the memory circuit 36, the data is temporarily stored in the first separate memory circuit 140 by the first separate keyboard 116. (It is to be understood that the data may be input to the second separate memory circuit 144 by the second separate keyboard 124 mounted in the endoscope camera 122). When the endoscope 100 is connected to the light supply apparatus 132 of the present invention and the first data transfer switch 120 is set to on, the data stored in the first separate memory circuit 140 is transferred to the memory circuit 36 mounted in the light supply apparatus 132 through the external connection wire 142. The following operation is the same as that described above, and the data stored in the second separate memory circuit 144 of the endoscope 122 is transferred to the memory circuit 36 of the light supply apparatus 132.

According to the another embodiment of the construction as described above, in addition to the keyboard 20, the memory circuit 36 and the indicator 44 mounted on the light supply apparatus 132, the keyboards 116 and 124, the memory circuits 140 and 144, and the indicators 118 and 126 are also mounted on the endoscope 100 and the endoscope camera 122. The user may select any of these keyboards to input the frame number and the corresponding data to be recorded and the input of the data may be immediately confirmed by the indicator which responds to the keyboard selected. The endoscope 100, the endoscope camera 122, and the light supply apparatus 132 may be used in combination with the conventional devices, offering a broad latitude of application.

Although the present invention has been shown and described with respect to particular embodiments, various changes and modifications which are obvious to a person skilled in the art to which the invention pertains are deemed to lie within the spirit, scope, and contemplation of the invention. For example, when the memory circuit is an involatile memory, the power source may be turned off after inputting the data and before recording the data so that the energy consumption of the power source such as an electric cell may be minimized. Further, the means for inputting the frame number and the corresponding data in the memory circuit is not limited to the keyboard but may be a magnetic card reader, a voice recognition device, an optical letter reading device and so on. Further, the frame number-setting dial and the display window need not be mounted, and the keyboard and the frame number indicator may incorporate these functions, respectively. In this case, when a desired frame number is set using the keyboard, the display of the frame number indicator flashes. Thereafter, when the film frame comes to the specified position corresponding to the frame number set, the flashing automatically stops. If a further mechanism is included for automatically feeding the film to the next frame when the data recording is completed, it is not necessary to set the frame number for every recording operation so that the data recording may be performed faster.

Further, the frame number and the data may be displayed within the field of view of the finder of the camera. Further, the memory circuit may be so constructed as to be capable of storing the frame number whose data has been already recorded. A mechanism for informing the user by sound and/or light signal when a film frame on which data has been already completely recorded has been erroneously positioned for further data recording may be incorporated and another mechanism for locking the recording starting button 26 may also be incorporated. With such a construction, double recording of data may certainly be prevented.

What is claimed is:

1. A data recording device for recording desired data on a desired frame of a film used in a photographic device for a photographing operation, said data recording device comprising:

data generating means having an output for generating data corresponding to a frame of the film and recording data;

memory means having an output and an input connected to the output of said data generating means for storing the data output from said data generating means;

frame-specifying means having an output for outputting a signal corresponding to a desired frame selected from the film frames;

film-driving means having an input connected to the output of said frame-specifying means for positioning the desired frame to a predetermined position in response to the signal from said frame-specifying means;

read-out means having an output and inputs connected to the outputs of said memory means and said frame-specifying means, respectively, for reading out desired recording data from said memory means in response to the signal output from said frame-specifying means;

data recording means having an input connected to the output of said read-out means for copying the recording data output from said read-out means onto the desired frame of the film; and means for displaying at least the recording data read out by said read-out means.

2. A data recording device according to claim 1, further comprising a recording starting button connected to said data recording means, at least said data recording means being operative independently of the photographing operation of the photographic device by said recording starting button.

3. A data recording device according to claim 1 or 2, wherein at least said memory means, said read-out means and said data recording means are built into said photographic device.

4. A data recording device according to any one of claims 1, 2 or 3, wherein said photographic device comprises a single lens reflex camera.

5. A data recording device according to any one of claims 1, 2 or 3, wherein said photographic device comprises an endoscope photographic device including a camera and an endoscope.

6. A data recording device according to claim 1 or 2, wherein said data generating means comprises a keyboard.

7. A data recording means according to claim 1 or 2, wherein said data generating means comprises a plurality of keyboards connected parallel with each other, and said recording data and data corresponding to a frame are input to said memory means by operating one of said plurality of keyboards.

* * * * *